(12) United States Patent
Tippit, Jr. et al.

(10) Patent No.: US 8,746,070 B2
(45) Date of Patent: Jun. 10, 2014

(54) PHASED ARRAY ULTRASONIC EXAMINATION SYSTEM AND METHOD

(75) Inventors: William Carol Tippit, Jr., Houston, TX (US); C. Michael Lewis, Houston, TX (US)

(73) Assignee: Tejas Testing & Inspection, Inc., Houston, TX (US)

( * ) Notice: Subject to any disclaimer, the term of this patent is extended or adjusted under 35 U.S.C. 154(b) by 313 days.

(21) Appl. No.: 13/440,543

(22) Filed: Apr. 5, 2012

(65) Prior Publication Data

US 2012/0255360 A1    Oct. 11, 2012

Related U.S. Application Data

(60) Provisional application No. 61/516,803, filed on Apr. 8, 2011.

(51) Int. Cl.
*G01N 29/04*    (2006.01)

(52) U.S. Cl.
USPC ............................................. 73/620; 73/622

(58) Field of Classification Search
USPC ........... 73/620, 592, 602, 622, 626, 628, 632, 73/633, 644
See application file for complete search history.

(56) References Cited

U.S. PATENT DOCUMENTS

| | | | |
|---|---|---|---|
| 4,195,530 A | 4/1980 | Ross et al. | |
| 4,319,490 A | 3/1982 | Hartmann, Jr. | |
| 4,718,277 A * | 1/1988 | Glascock | 73/622 |
| 5,549,004 A | 8/1996 | Nugent | |
| 5,578,758 A | 11/1996 | Havira et al. | |
| 6,651,502 B1 | 11/2003 | Davis | |
| 6,957,583 B2 | 10/2005 | Tooma et al. | |

(Continued)

FOREIGN PATENT DOCUMENTS

| CN | 10/1625337 A | | 1/2010 |
|---|---|---|---|
| CN | 201844727 | * | 5/2011 |

(Continued)

OTHER PUBLICATIONS

Olympus: "Phased Array Probes and Wedges" (Olympus Catalog—retrieved on Feb. 17, 2012) http://www.olympus-ims.com/data/File/PA_Probes/PA-Peobe_Catalog.en.

(Continued)

*Primary Examiner* — J M Saint Surin
(74) *Attorney, Agent, or Firm* — Gary L. Bush; Andrews Kurth LLP

(57) ABSTRACT

A method and apparatus for phased array ultrasound testing of piping that complies with present-day codes but allows more thorough flaw detection capability. A tapered wedge with a concave face is calibrated by submerging the wedge under sonic coupling fluid, thereby allowing sonic coupling of the concave wedge face to a flat reference plate with minimal error. The flaw detector is configured to display A-scan and S-scan data concurrently and to sweep between 30-70 degrees. A-scan data corresponding with conventional preferred inspection incidence angle is selected, and reject levels are set to 0% to meet current inspection standards. S-scan data allows for detection of flaws that might otherwise be undetectable using only A-scan data. A palette adjustment feature remaps the colors assigned to lower intensity return values so that they are not displayed on the S-scan, thereby de-cluttering sectorial data without filtering A-scan data.

11 Claims, 5 Drawing Sheets

(56) References Cited

U.S. PATENT DOCUMENTS

| | | | |
|---|---|---|---|
| 7,165,453 | B2 | 1/2007 | Flora et al. |
| 7,293,461 | B1 | 11/2007 | Girndt |
| 7,581,444 | B2 * | 9/2009 | Maurer et al. .................. 73/597 |
| 7,861,591 | B2 * | 1/2011 | Rath et al. ....................... 73/592 |
| 7,874,212 | B2 | 1/2011 | Yamano |
| 7,975,549 | B2 | 7/2011 | Fetzer et al. |
| 8,490,490 | B2 * | 7/2013 | Yamano ........................ 73/602 |
| 8,495,915 | B2 * | 7/2013 | Yamano ........................ 73/602 |
| 2013/0333429 | A1 * | 12/2013 | Mochizuki ...................... 72/41 |
| 2014/0050046 | A1 * | 2/2014 | Sinha et al. ..................... 367/7 |

FOREIGN PATENT DOCUMENTS

| | | |
|---|---|---|
| CN | 10/2175766 A | 9/2011 |
| FR | 2796153 A1 | 1/2001 |
| FR | 2891909 A1 | 4/2007 |
| JP | 571469673 A | 10/1982 |
| JP | 6288996 A | 10/1994 |
| JP | 2006/194591 A | 7/2006 |
| JP | 200619459 * | 7/2006 |
| JP | 2007/251505 A | 9/2007 |
| SU | 497514 A1 | 12/1975 |
| SU | 1216724 A | 3/1986 |
| SU | 1244582 A2 | 7/1986 |
| WO | WO 99/13327 A1 | 3/1999 |
| WO | WO 2009/041139 A1 | 4/2009 |

OTHER PUBLICATIONS

Olympus: "Intro to Ultrasonic Testing" (info retrieved Mar. 5, 2012) http://www.olympus-ims.com/en/ndt-tutorials/intro/ut/.

Olympus: "The Standard in Phased Array, Redefined" (Phased Array Flaw Detector—OmniScan® MX2 http://www.plympus-ims.com.

Nelligan, T. and Kass, D.: "Intro to Ultrasonic Phased Array" (retrieved on Feb. 27, 2012) www.olympus-ims.com/en/ultrasonics/intro-to-pa/.

* cited by examiner

PHASED ARRAY ULTRASONIC EXAMINATION SYSTEM AND METHOD

CROSS REFERENCE TO RELATED APPLICATION

This application is based upon provisional application 61/516,803 filed on Apr. 8, 2011, which is incorporated herein by reference and the priority of which is claimed.

BACKGROUND OF THE INVENTION

1. Field of the Invention

The present disclosure relates to a system and method for examining and testing solid objects using non-destructive ultrasonic phased arrays. More particularly, the present disclosure relates to a system and method for examining and testing seamless mechanical tubing and piping.

2. Background Art

Solid objects such as mechanical equipment may sometimes have physical flaws. Flaws may either occur during the manufacturing stage or at a later time due to external factors. It is important to find such flaws prior to the mechanical equipment being put into use. Otherwise, the mechanical equipment may fail causing loss of property or personal injury. However, such flaws are often undetectable via visual inspection. Thus, there is a need for a method which may be used to detect such flaws so that they may be detected in a timely manner and problems prevented.

Much of the tubular steel used in the petrochemical industry is inspected using a process commonly referred to as A-scan examination. In the A-scan examination process, ultrasonic waves are introduced into the outer surface of the pipe at a prescribed angle. Pulses of sound are introduced into the part being inspected through a probe containing a single crystal element (i.e., monocrystal), referred to as a transducer. Then, the echo returned is analyzed. The return echo is a function of the geometry of the material. When there is a flaw, the geometry of the material is internally changed, which is indicated by the return echo of the A-scan examination process. However, if the flaw in the material is not generally perpendicular to the sound path, the flaw may go undetected.

To control the direction of the sound, a plastic wedge is fastened to the face of the transducer, which is then connected to the ultrasonic flaw detector via coaxial cable. This wedge is formed at an angle so that the sound enters the steel at that specific angle. The angle used in the A-scan examination process is typically a 45 degree angle. However, a single 45 degree angle cannot detect all of the flaws due to geometry aspects of the ultrasonic waves. For example, if a flaw in the pipe is itself angled at 45 degrees, the A-scan examination process will not detect it.

The traditional A-scan flaw detectors cannot electronically control the angle at which the sound is projected. The angle of sound cannot be changed without removing the wedge and replacing it with another wedge that has a different angular relationship between the ultrasonic wave and the structure being measured.

Weld joints may be particularly problematic. Welds are known to be subject to many types of defects that can orient themselves in unpredictable ways. Accordingly, weld inspections are generally more rigorous and meticulous than inspections performed on raw materials, such as tubing.

Phased Array Ultrasonic Testing ("PAUT") is a newer technology that is being used in a variety of industries to verify the integrity of welds. A PAUT scan is typically referred to as an "S-scan."

Unlike an A-scan flaw detector that uses a single-element transducer, a phased array system uses transducers with multiple emission elements (i.e., 8, 16, 32, 64, 128, etc.) to create sound waves. Phased array technology harnesses the physics of constructive and destructive wave interference. In a phased array methodology, individual piezoelectric elements are excited in a controlled manner such that the direction of the combined wavefront is easily controllable without any physical movements or changes of the operator. The sound waves in a phased array pulse may be steered through a multitude of angles in a similar amount of time that a traditional A-scan flaw detector scans only a single angle. Scanning at many angles enhances the probability of finding defects in materials.

Although PAUT is often used in weld inspection, it has not found common use for inspection of raw tubular stock, particularly due to several shortcomings. Accordingly, it is desirable to provide a method and apparatus for phased array ultrasound testing of tubular goods and other mechanical equipment that overcomes such shortcomings so as to provide more effective and economical flaw detection.

3. Identification of Objects of the Invention

A primary object of the invention is to provide a method and apparatus for phased array ultrasound inspection of tubular goods that satisfies present A-scan inspection standards.

Another object of the invention is to provide a method and apparatus for effective calibration of phased array ultrasound inspection systems when used with tubular goods.

SUMMARY OF THE INVENTION

The objects described above and other advantages and features of the invention are incorporated in a method and a system that provides for adapting phased array ultrasound testing techniques for inspecting raw material in bulk, particularly seamless mechanical tubing and piping, which complies with present-day industry codes and standards but allows for much more robust and thorough flaw detection capability.

A tapered wedge with a concave face to match pipe outer diameter is mounted to a multi-element phased array transducer, which in turn is connected to a phased array ultrasound testing flaw detector, which measures, monitors and analyzes the signals generated and received by the transducer. The transducer transmits the sound wavefronts through the test sample at prescribed angles and measures the time and intensity of the echoes. The flaw detector is preferably capable of simultaneously displaying S-scan and A-scan images.

Prior to testing, the flaw detector is calibrated by submerging the wedge under a sonic coupling fluid, thereby allowing sonic coupling of the concave wedge face to a flat reference plate with minimal error.

The flaw detector is configured to display the A-scan on-screen concurrently with the S-scan. The flaw detector is set so that it produces a beam which sweeps from 30 degrees to 70 degrees through the material to be tested. A-scan data that corresponds with the traditional preferred inspection incidence angle is selected, and reject levels are set to 0% to meet current inspection standards. The wedge is placed on the test piece and then moved spirally in a circumferential direction to detect longitudinal defects. The inspection is then performed in the opposite direction, resulting in a complete bi-directional circumferential inspection. Additionally, to further ensure a complete and effective inspection, the scanning is preferably performed axially. The S-scan data, displayed concurrently with the A-scan data for the preferred incidence angle, allows for detection of flaws that might otherwise be undetectable using only A-scan data. A palette adjustment feature of the flaw detector is utilized to remap the colors assigned to lower intensity return values so that they are not displayed on the S-scan. The result de-clutters S-scan data without filtering A-scan data, allowing the operator to more readily identify flaws using S-scan data while concurrently meeting A-scan inspection code requirements.

BRIEF DESCRIPTION OF THE DRAWINGS

The invention is described in detail hereinafter on the basis of the embodiments represented in the accompanying figures, in which.

DESCRIPTION OF THE PREFERRED EMBODIMENT OF THE INVENTION

The current disclosure describes a method and apparatus for adapting PAUT for use in inspecting raw material in bulk, particularly seamless mechanical tubing and piping, which complies with present-day industry codes and standards (that currently provide only for A-scan processes) but allows for much more robust and thorough flaw detection capability. The present disclosure exceeds current code and industry standards by providing exceptional flaw detection not otherwise available using known methods.

The basic equipment required to practice the invention includes a PAUT flaw detector, a PAUT transducer, and an angled wedge. Currently, there are no known engineering standards developed by ASME, ASIM or API for the application of PAUT to bulk tubular goods. Although some adjustments will be made to the equipment for adapting it for use with bulk tubular goods, many of the requirements of ASTM E2700 for welds remain applicable.

The flaw detector of the present disclosure is a phased array unit, such as an Olympus 1000i, which preferably complies with the specifications set forth in Section 7 of ASTM E2700. A multi-element phased array transducer is connected to the flaw detector, which measures, monitors and analyzes the signals generated and received by the transducer. The transducer transmits the sound wavefronts through the test sample at prescribed angles and measures the time and intensity of the echoes. The flaw detector is capable of supporting at least one 16-element transducer in a one-dimensional array, although larger arrays may be used as appropriate.

Figure 1:
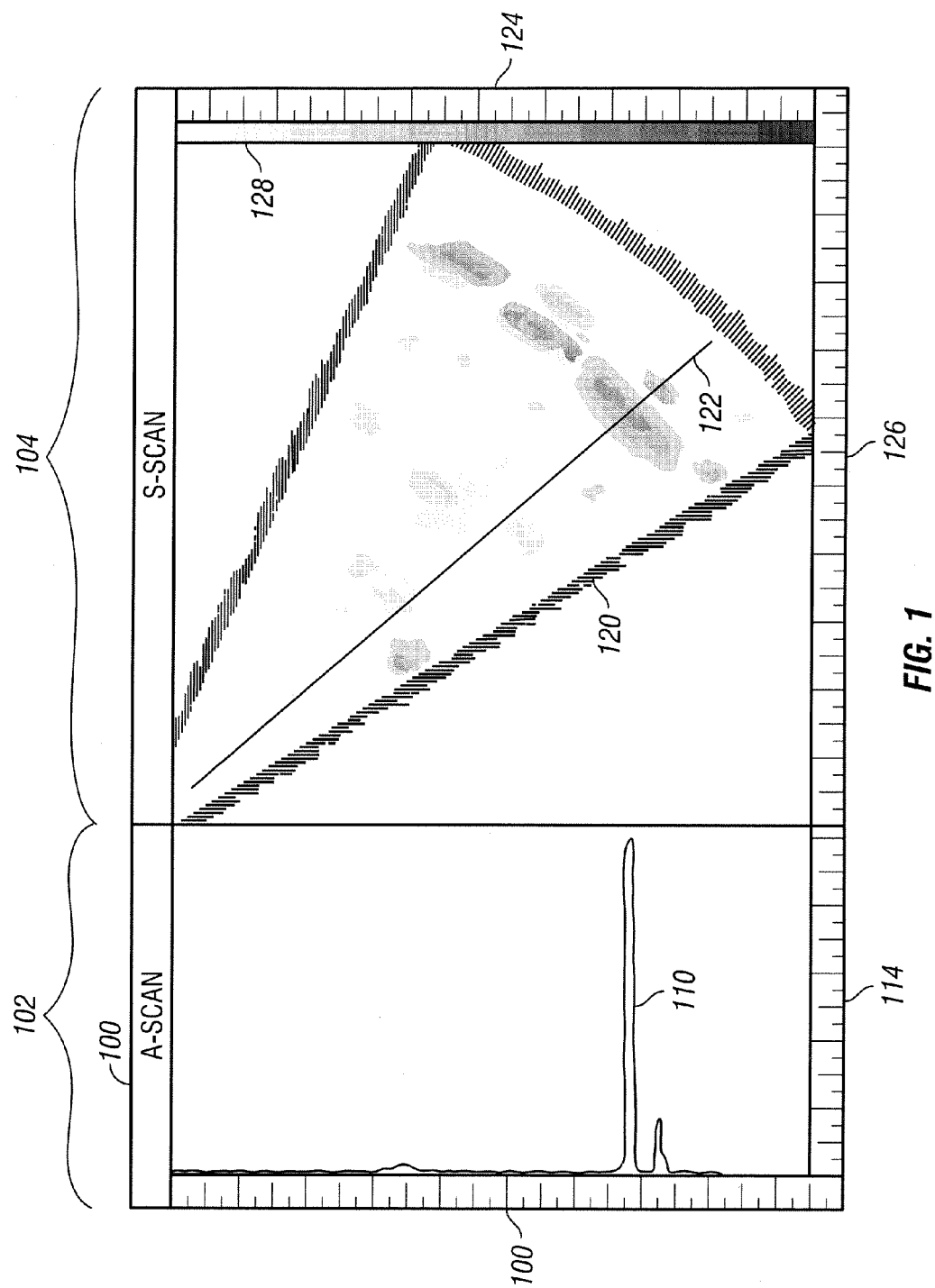
FIG. 1 illustrates the display screen of a PAUT flaw detector during inspection of a cylindrical tube according to a first embodiment of the invention, showing an A-scan display for satisfying current inspection standards and an S-scan display for providing more robust inspection data.
Figure 2A:
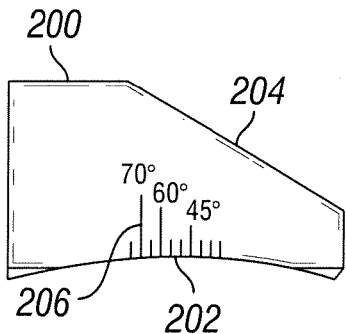
FIG. 2A is a side elevation of a wedge used for circumferential phased array ultrasound testing of cylindrical tubular goods according to a preferred embodiment of the invention, showing a concave bottom surface for conforming with pipe outer diameter.
Figure 2B:
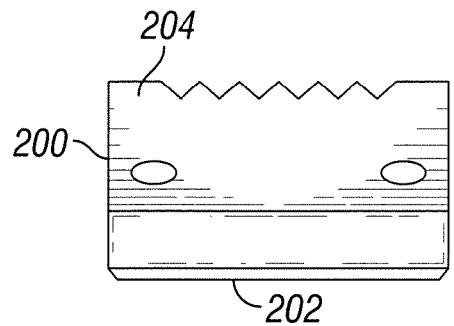
FIG. 2B is a front elevation of the wedge of FIG. 2A, showing a tapered upper surface for coupling to a transducer probe.
Figure 2C:
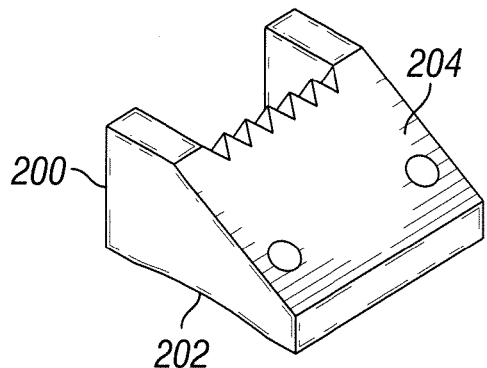
FIG. 2C is a perspective view of the wedge of FIG. 2A from above.
Figure 2D:
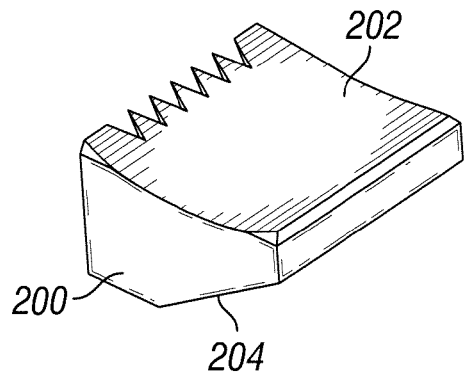
FIG. 2D is a perspective view of the bottom surface of the wedge of FIG. 2A.
Figure 2E:
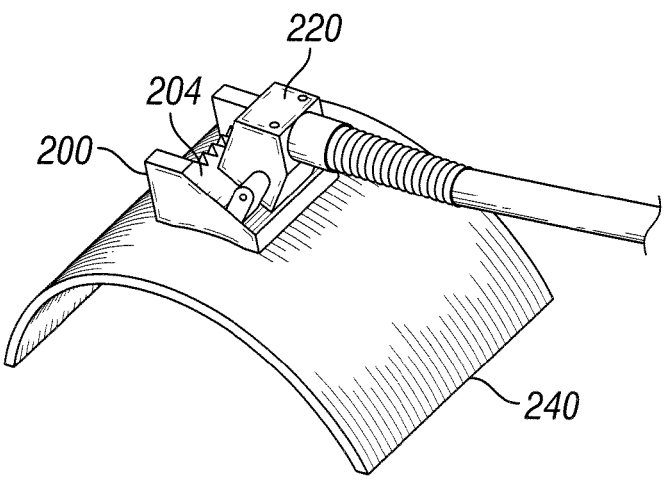
FIG. 2E is perspective view of the wedge of FIG. 2A during testing, showing a transducer probe mounted to the upper tapered surface and the bottom surface placed against cylindrical tubular stock for circumferential scanning.
Figure 3A:
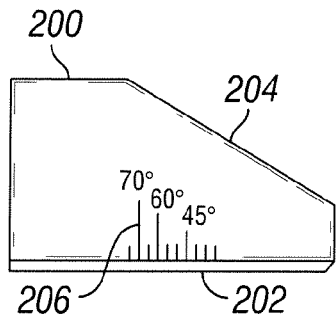
FIG. 3A is a side elevation of a wedge used for axial phased array ultrasound testing of cylindrical tubular goods according to a preferred embodiment of the invention, showing a concave bottom surface for conforming with pipe outer diameter.
Figure 3B:
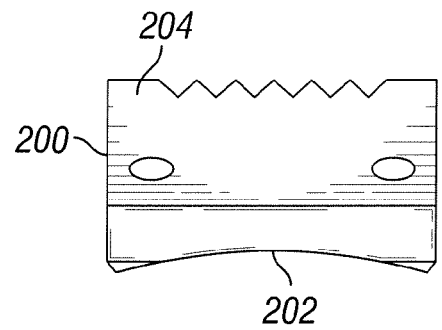
FIG. 3B is a front elevation of the wedge of FIG. 3A, showing a tapered upper surface for coupling to a transducer probe.
Figure 3C:
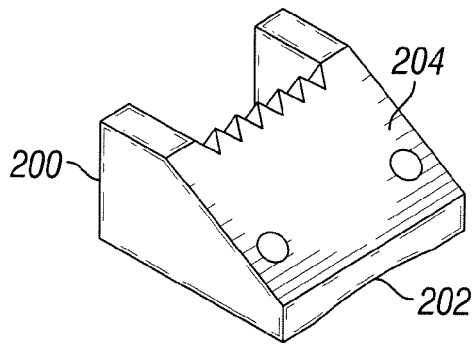
FIG. 3C is a perspective view of the wedge of FIG. 3A from above.
Figure 3D:
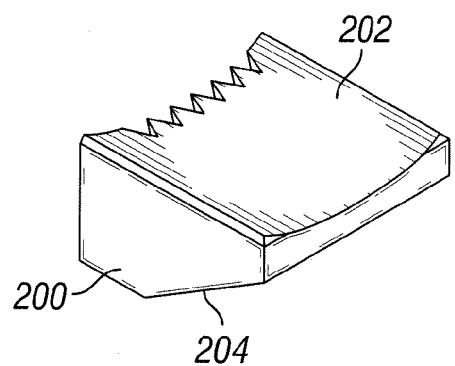
FIG. 3D is a perspective view of the bottom surface of the wedge of FIG. 3A.
Figure 3E:
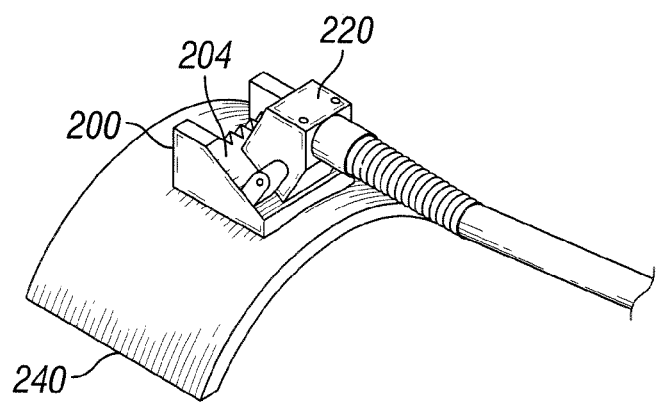
FIG. 3E is perspective view of the wedge of FIG. 3A during testing, showing a transducer probe mounted to the upper tapered surface and the bottom surface placed against cylindrical tubular stock for axial scanning.

The flaw detector is preferably capable of simultaneously displaying S-scan and A-scan images such as illustrated in FIG. 1. The display screen 100 of a PAUT flaw detector includes an A-scan window 102 on the left side and an S-scan window 104 on the right side. The A-scan window 102 shows a waveform 110 that represents the path of an ultrasound wave at single incident beam angle, while the S-scan window 104 shows combined sectorial scan data 120 for a sweep of the incident beam through a range of angles. The A-scan data displayed (i.e., the incident beam angle) is selectively controlled by the user and is indicated in the S-scan display 104 by a cursor, commonly referred to as a focal law selector 122. The sectorial scan data 120 is generated by electronically steering the incident sound wave through a sequence of angles and plotting the echo response at each angle, with intensity depicted by color, thereby presenting a cross-sectional picture of the inspected area of the test piece.

The vertical scale 112 at the left of the A-scan display represents depth, and the horizontal scale 114 at the bottom of the A-scan display indicates the amplitude of the received echo. The vertical and horizontal scales 124, 126 at the bottom and right of the S-scan display 104 indicate distance, and the color spectrum legend 128 correlates echo amplitude to the sectorial scan data 120.

FIGS. 2A-2E and 3A-3E illustrate a contoured wedge 200 according to a preferred embodiment of the invention for use in PAUT pipe inspection. Wedge 200 of FIGS. 2A-2E is contoured for circumferential scanning, and wedge 200 of FIGS. 3A-3E is contoured for axial scanning. Wedge 200 has a bottom surface 202 that is contoured with a concavity so as to match the outside diameter ("OD") curvature of the material 240 to be inspected. Wedge 200 includes an upper surface 204 that is angled in a manner to allow the transducer probe 220 to be mounted thereon (FIGS. 2E, 3E) so as to produce a 30 degree to 70 degree sweep of the material being tested. Such range of angles advantageously allows for generation of shear waves. Hardened steel wear inserts may optionally be used to preserve the natural shape of the wedge throughout scanning process. Ideally, at no time during scanning is the surface of the wedge further than 0.5 mm of the material being tested. Indicia 206 indicating the exit points of sound are an important part of the design of wedge 200.

Ultrasound flaw detectors are typically calibrated using standards in the shape of flat plates, typically referred to as "IIW blocks." While such reference blocks are ideal for flat-bottom wedges, they are not particularly suitable for calibrating wedges having concave bottom surfaces, because an air gap between the bottom surface of the wedge and the reference block prevents adequate sonic coupling. Although the probe can first be calibrated using a flat-bottom wedge, and then the required curved wedge substituted for the flat wedge during testing, such a calibration technique is undesirable because the complete flaw detector system used for testing is not the complete system that was actually calibrated to the standard. Therefore, the method according to a preferred embodiment of the invention includes a unique method for calibrating flaw detector systems using off-the-shelf flat IIW reference blocks with curved wedges.

Figure 4:
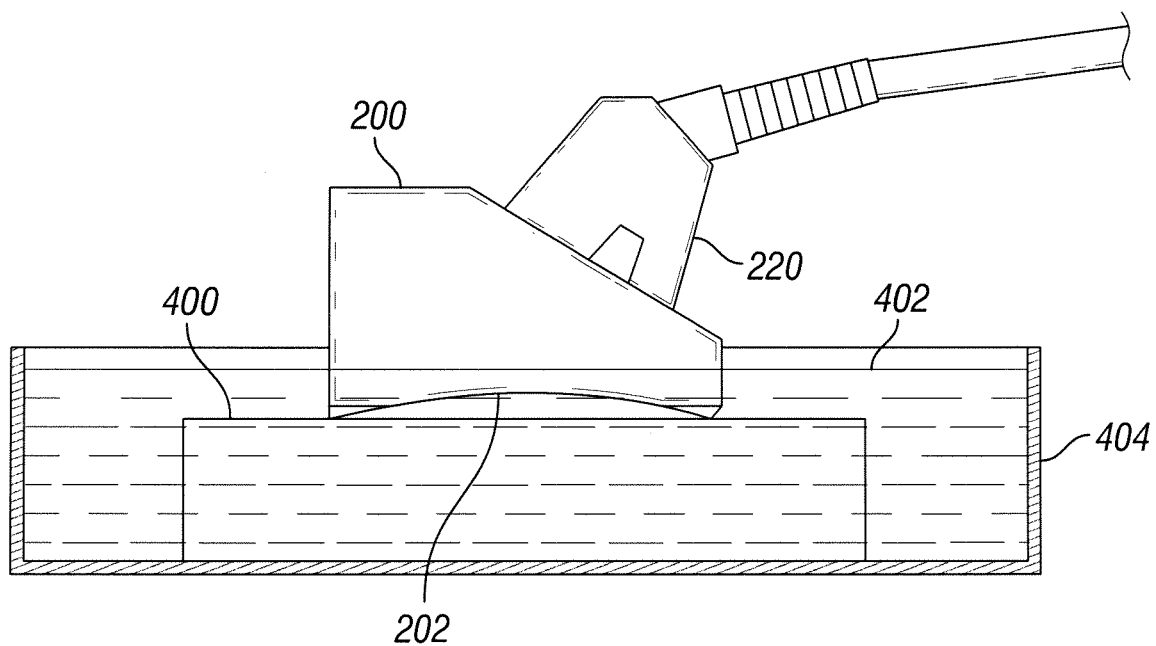
FIG. 4 is a side elevation in partial cross section of the calibration arrangement for a curved wedge using a flat plate calibration standard wherein the wedge is sonically coupled to the calibration plate in a fluid-bath.

FIG. 4 illustrates the calibration method. The flat-plate reference block 400 is submerged in sonic coupling liquid or gel 402, such as glycerin or water, in a shallow pan or dish 404. The bottom of the curved wedge 200 is also immersed in couplant 402, with care to ensure that all air pockets are purged and not entrapped under the concave bottom surface 202 of the wedge. In this manner, refraction within the gap formed between wedge 200 and reference block 400 is minimized so as to allow calibration within acceptable tolerances.

A second calibration standard, typically a notched sample of similar OD, ID, and material grade as the pipe to be inspected is also preferably used. Notches or side-drilled holes (SDH) are made to represent defects and verify functionality of the system. The notches or SDH may be of 3%, 5%, 10% or 12.5% of the total thickness of the material tube tested. The equipment is standardized prior to the inspection to comply with the requirements in ASTM E2700 Section 8. A distance amplitude curve at approximately 80% full-screen height is plotted to comply with requirements set forth in customer procedures. A minimum of 6 dB shall be added for increased scanning sensitivity.

The flaw detector is configured to display the A-scan 110 on-screen concurrently with the S-scan 120. The flaw detector should be set so that it produces a beam which sweeps from 30 degrees to 70 degrees through the material to be tested. The beam should be set so that as it oscillates between the 30 degrees and 70 degrees in increments not to exceed 2 degrees. The focal depth of the beam should preferably be about twice the thickness of the tubing wall.

According to present-day industry inspection standards, which provide only for A-scan pipe inspection, the preferred angle at which the sound waves should be introduced into the pipe wall during a circumferential A-scan ultrasound test is determined by the inverse sine of the inner diameter divided by the outer diameter. According to the present invention, the focal law selector 122 of the PAUT flaw detector is adjusted so that the A-scan window 102 displays its readings 110 for this preferred angle, rounded down to the nearest whole number. Unless otherwise specified, the allowable range for this preferred incidence angle is approximately 30-45 degrees. If the calculated preferred angle is less than 30 degrees, then a straight beam inspection is preferred over shear wave inspection. On the other hand, if the calculated preferred angle is over 45 degrees, the flaw detector is set to 45 degrees. By setting the focal law selector 122 of the PAUT flaw detector to the preferred incidence angle for A-scan testing and displaying the corresponding A-scan waveform 110, the present method according to the preferred embodiment of the invention satisfies current industry inspection standards yet provides much more robust sectorial scan data 120 for detecting flaws.

In a preferred embodiment, the surface condition of the material 240 to be inspected shall be a smooth finish of at least 250 RMS (6.3 µM). The material shall be cleaned so that it is free of loose scale, dirt, chemicals, and anything else that may inhibit proper coupling of the wedge. The test piece 240 is coated with a layer of a wetting or thickening agent 402 so that when wedge 200 is placed against the material, no air remains between wedge 200 and test piece 240 for proper sonic coupling.

Once the flaw detector, transducer 220, wedge 200, and test piece 240 are prepared and preliminarily tested, inspection begins. The wedge 200 is placed on one part of the tube or pipe 240 and then moved spirally in a circumferential direction to detect longitudinal defects at a rate not to exceed 6 inches per second. The scanning is done so that there is at least a 10% overlap between scan paths to ensure complete coverage and optimal results. The inspection is then performed in the opposite direction, resulting in a complete bi-directional circumferential inspection. Additionally, to further ensure a complete and effective inspection, the scanning is preferably performed axially. A contoured wedge such as shown in FIGS. 3A-3E is used when scanning axially.

As the scanning is performed during inspection, results based on the reflection of sound are transmitted through wedge 200 and transducer 220 back to the flaw detector. The flaw detector displays the A-scan and S-scan phased array readings 110, 120 simultaneously. Evaluation of indications observed from the A-scan 110 and/or S-scan 120 are performed with the dB setting returned to the reference level as noted during the initial standardization. The initial evaluation sets the focal law selector 12 to display the A-scan data 110 corresponding to the calculated preferred incidence angle for traditional A-scan testing. If the indication does not exceed the reference amplitude using the preferred angle, then the focal law selector 122 is adjusted to display the incidence angle producing the maximum amplitude of sound reflection. If the amplitude of sound reflection for the material exceeds the reference amplitude at an angle other than the preferred angle, it indicates there is a flaw in the material. As an operator might note, some flaws that are not detectable by the A-scan technique are readily detectable by the PAUT scan technique of the present invention.

According to the current A-scan industry standards for inspecting tubular goods, the rejection level setting of the flaw detector must be set to 0%. Increasing the rejection level reduces low-level noise, but conventional wisdom and code require that rejection level be set to 0% and the operator to discern between noise and flaws in the A-scan data 110. When S-scan data 120 is viewed with the rejection level setting at 0%, low-level noise tends to clutter the display as illustrated in FIG. 1. Such a cluttered S-scan display 104 makes it difficult for one to identify flaws. Nevertheless, the rejection level setting should remain set at 0% so that the A-scan data 110 is code-compliant.

Figure 5:
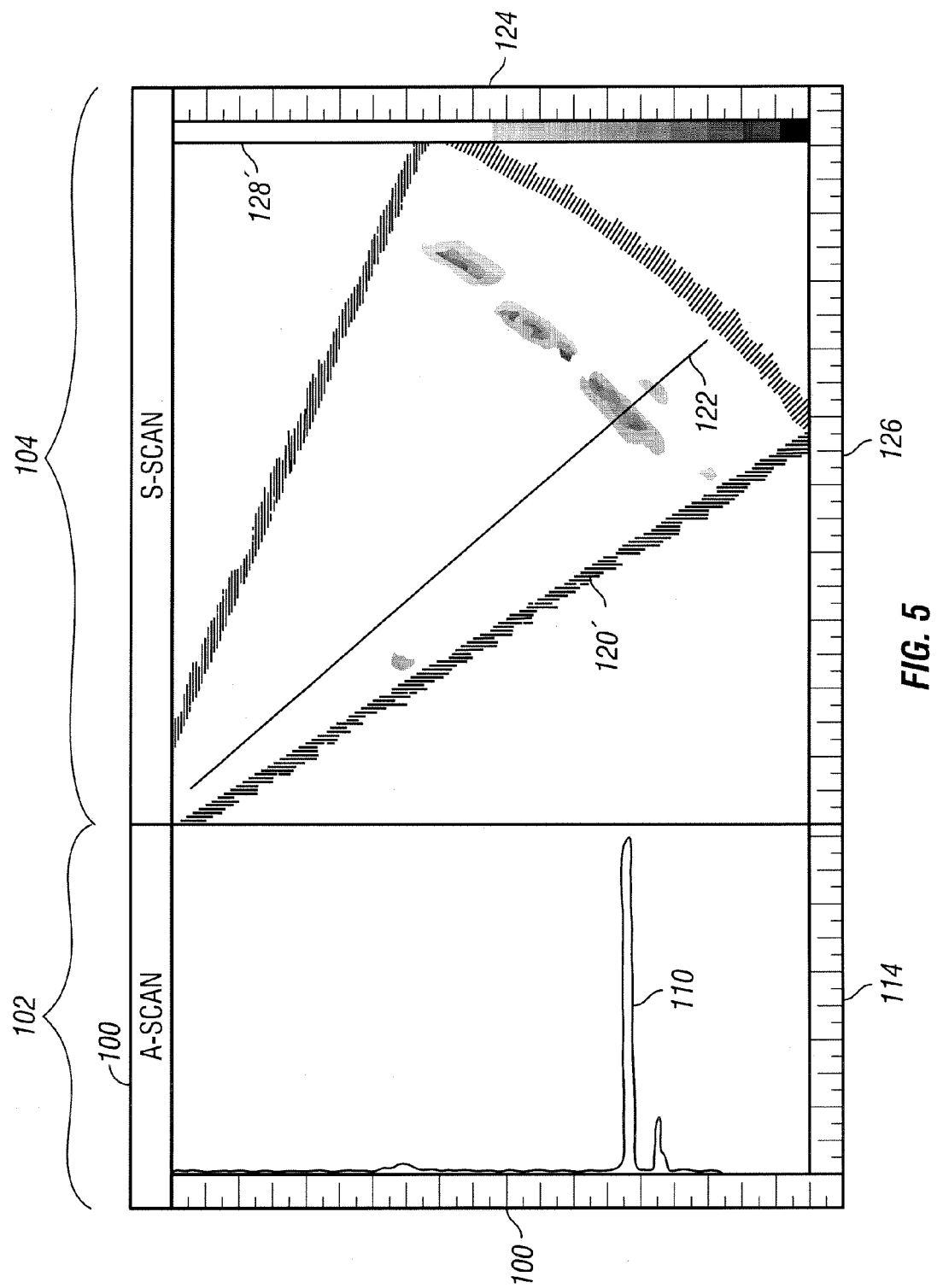
FIG. 5 illustrates the display screen of the PAUT flaw detector of FIG. 1 during inspection of cylindrical tubular goods according to a preferred embodiment of the invention, showing a S-scan display with a remapped palette for reducing echo and noise clutter.

FIG. 5 illustrates a preferred embodiment of the invention that de-clutters the S-scan data 120 while leaving the rejection level set to 0%. A palette adjustment feature of the flaw detector is utilized to remap the colors assigned to lower intensity return values so that they are not displayed on the S-scan 120. For example, the legend 128' of FIG. 5 has shifted the color spectrum toward the higher-intensity values than the color spectrum legend 128 of FIG. 1. The result de-clutters S-scan data 120' of FIG. 5 as compared to the S-scan data 120 of FIG. 1 without filtering A-scan data 110. Such color remapping technique allows the operator to more readily identify flaws using S-scan data 120 while concurrently meeting A-scan inspection code requirements.

The Abstract of the disclosure is written solely for providing the United States Patent and Trademark Office and the public at large with a way by which to determine quickly from a cursory reading the nature and gist of the technical disclosure, and it represents solely a preferred embodiment and is not indicative of the nature of the invention as a whole.

While some embodiments of the invention have been illustrated in detail, the invention is not limited to the embodiments shown; modifications and adaptations of the above embodiment may occur to those skilled in the art. Such modifications and adaptations are in the spirit and scope of the invention as set forth herein:

What is claimed is:

1. A method for inspecting a cylindrical tubular structure (240) characterized by an inside diameter and an outside diameter, the method comprising the steps of:
    providing a phased array ultrasound flaw detection system including a detector electrically connected to a transducer (220), said transducer mounted to an upper surface of a wedge (200), said wedge having a lower concave surface (202);
    providing a reference plate (400) having a flat surface;
    abutting said concave surface of said wedge against said flat surface of said reference plate thereby defining an interstice between said concave surface and said flat surface;
    filling said interstice with a sonic couplant;
    calibrating said flaw detection system while said interstice is filled with said sonic couplant;
    coating said structure with said sonic couplant;
    disposing said concave surface of said wedge against said coated structure at a first point;
    introducing an ultrasound wavefront generated at said transducer through said wedge into said coated structure;
    sweeping said ultrasound wavefront through a plurality of incidence angles including a preferred incidence angle that is defined by the inverse sine of said inside diameter divided by said outside diameter;
    measuring an echo return signal of said ultrasound wavefront received at said transducer at each of said plurality of incidence angles;
    displaying all of said measured echo return signal received at said preferred incidence angle in an A-scan format (110) on said detector while simultaneously displaying at least part of said measured echo return signals received at all of said plurality of incidence angles in an S-scan format (120) on said detector; then
    moving said concave surface of said wedge against said coated structure to a second point; and
    repeating said steps of introducing, sweeping, measuring, and displaying at said second point.

2. The method of claim 1 further comprising the step of:
    submerging said interstice in said sonic couplant.

3. The method of claim 1 further comprising the step of:
    assigning a palette setting of said detector so as to cause any of said measured echo return signals that have low amplitude to not be displayed in said S-scan format (120') on said detector.

4. The method of claim 1 further comprising the step of:
    moving said concave surface of said wedge circumferentially with respect to said structure from said first point to said second point.

5. The method of claim 1 further comprising the step of:
    moving said concave surface of said wedge axially with respect to said structure from said first point to said second point.

6. The method of claim 1 further comprising the step of:
    sweeping said ultrasound wavefront through a plurality of incidence angles between 30 and 70 degrees.

7. The method of claim 1 further comprising the step of:
    sweeping said ultrasound wavefront through a plurality of incidence angles between 30 and 60 degrees.

8. A method for inspecting a cylindrical tubular structure (240) characterized by an inside diameter and an outside diameter, the method comprising the steps of:
    providing a phased array ultrasound flaw detection system including a detector electrically connected to a transducer (220);
    mounting said transducer to an upper surface of a first wedge (200), said first wedge having a lower concave surface (202) oriented for circumferential scanning with respect to said structure;
    providing a reference plate (400) having a flat surface;
    abutting said concave surface of said first wedge against said flat surface of said reference plate thereby defining a first interstice between said concave surface of said first wedge and said flat surface;
    submerging so as to fill said first interstice with a sonic couplant;
    calibrating said flaw detection system while said first interstice is filled with said sonic couplant; then
    coating said structure with said sonic couplant;
    disposing said concave surface of said first wedge against said coated structure; and
    while moving said first wedge in a circumferential direction around said structure,
        introducing ultrasound wavefronts generated at said transducer through said first wedge into said coated structure,
        sweeping said ultrasound wavefronts through a plurality of incidence angles including a preferred incidence angle that is defined by the inverse sine of said inside diameter divided by said outside diameter,
        measuring echo return signals of said ultrasound wavefronts received at said transducer at each of said plurality of incidence angles, and
        displaying all of said measured echo return signals received at said preferred incidence angle in an A-scan format (110) on said detector while simultaneously displaying at least part of said measured echo return signals received at all of said plurality of incidence angles in an S-scan format (120) on said detector.

9. The method of claim 8 further comprising the steps of:
    mounting said transducer to an upper surface of a second wedge (200), said second wedge having a lower concave surface (202) oriented for axial scanning with respect to said structure;
    abutting said concave surface of said second wedge against said flat surface of said reference plate thereby defining a second interstice between said concave surface of said second wedge and said flat surface;
    submerging so as to fill said second interstice with said sonic couplant;
    calibrating said flaw detection system while said second interstice is filled with said sonic couplant; then
    disposing said concave surface of said second wedge against said coated structure; and
    while moving said second wedge in a axial direction along said structure,
        introducing ultrasound wavefronts generated at said transducer through said second wedge into said coated structure, sweeping said ultrasound wavefronts through said plurality of incidence angles,
measuring echo return signals of said ultrasound wavefronts received at said transducer at each of said plurality of incidence angles, and
displaying said measured echo return signals on said detector.

10. The method of claim 8 further comprising the step of:
sweeping said ultrasound wavefronts through a plurality of incidence angles between 30 and 70 degrees.

11. The method of claim 8 further comprising the step of:
sweeping said ultrasound wavefronts through a plurality of incidence angles between 30 and 60 degrees.

\* \* \* \* \*